(12) United States Patent
Chen et al.

(10) Patent No.: US 9,453,243 B2
(45) Date of Patent: Sep. 27, 2016

(54) TRANSPORTATION DEVICE

(71) Applicant: Chien-Lung Chen, New Taipei (TW)

(72) Inventors: Chien-Lung Chen, New Taipei (TW); Cheng-Hsien Chen, Taipei (TW); Chang-Jer Wu, Taipei (TW); Han-Ning Huang, Taipei (TW)

(73) Assignee: CHIEN-LUNG CHEN, New Taipei (TW)

( * ) Notice: Subject to any disclaimer, the term of this patent is extended or adjusted under 35 U.S.C. 154(b) by 141 days.

(21) Appl. No.: 14/190,479

(22) Filed: Feb. 26, 2014

(65) Prior Publication Data

US 2014/0178974 A1 Jun. 26, 2014

Related U.S. Application Data

(63) Continuation-in-part of application No. 12/835,460, filed on Jul. 13, 2010, now Pat. No. 8,702,019.

(30) Foreign Application Priority Data

Jul. 14, 2009 (TW) .............................. 98123693 A

(51) Int. Cl.
| | | |
|---|---|---|
| *A62C 5/02* | (2006.01) | |
| *C12N 15/89* | (2006.01) | |
| *A61M 11/00* | (2006.01) | |
| *B05B 7/00* | (2006.01) | |
| *B05B 7/04* | (2006.01) | |
| *B05B 17/06* | (2006.01) | |
| *A61M 5/30* | (2006.01) | |
| *A61M 11/02* | (2006.01) | |
| *A61M 11/06* | (2006.01) | |
| *A61M 37/00* | (2006.01) | |

(52) U.S. Cl.
CPC .......... *C12N 15/895* (2013.01); *A61M 11/005* (2013.01); *B05B 7/0012* (2013.01); *B05B 7/0416* (2013.01); *B05B 7/0433* (2013.01); *B05B 17/0615* (2013.01); *A61M 5/30* (2013.01); *A61M 11/02* (2013.01); *A61M 11/06* (2013.01); *A61M 2037/0007* (2013.01)

(58) Field of Classification Search
CPC ... C12N 15/895; A61M 11/005; A61M 5/30; A61M 11/02; A61M 11/06; A61M 2037/0007; B05B 7/0012; B05B 7/0416; B05B 7/0433; B05B 17/0615
USPC ....... 239/310, 302, 307, 311, 337, 338, 344, 239/375, 396, 525, 526
See application file for complete search history.

(56) References Cited

U.S. PATENT DOCUMENTS

| | | | |
|---|---|---|---|
| 2,361,980 A * | 11/1944 | Tirrell ................. | A62D 1/0071 169/15 |
| 2,967,570 A | 1/1961 | Nurkiewicz | |
| 3,698,644 A | 10/1972 | Nystuen | |
| 3,701,482 A | 10/1972 | Sachnik | |

(Continued)

*Primary Examiner* — Justin Jonaitis
(74) *Attorney, Agent, or Firm* — Muncy, Geissler, Olds & Lowe, P.C.

(57) ABSTRACT

A transportation device, transporting a material to a target, includes an input module, a transmission module and an output module. The input module has a containing unit and at least one filter. The at least one filter is connected to the containing unit, and a carrier fluid and the material are stored in the containing unit. The transmission module is coupled to the at least one filter of the input module. The output module has a guiding unit, a throat portion, a first opening and a second opening. The throat portion is positioned between the first opening and the second opening. One end of the guiding unit is connected to the transmission module. The other end of the guiding unit has a guiding corner for connecting to the first opening. The material will enter the output module through the first opening and reaches the target through the second opening.

13 Claims, 14 Drawing Sheets

(56) References Cited

U.S. PATENT DOCUMENTS

| | | | |
|---|---|---|---|
| 4,391,390 A * | 7/1983 | Howard | B01D 15/04 137/205.5 |
| 6,113,004 A | 9/2000 | Steingass et al. | |
| 6,158,431 A | 12/2000 | Poole | |
| 7,638,332 B2 | 12/2009 | Lin et al. | |
| 2007/0164133 A1 | 7/2007 | Lin et al. | |

* cited by examiner

FIG. 12

TRANSPORTATION DEVICE

CROSS REFERENCE TO RELATED APPLICATIONS

This application is a Continuation-In-Part of U.S. application Ser. No. 12/835,460 filed on Jul. 13, 2010, which claims priority under 35 U.S.C. §119(a) on patent application No(s). 098123693 filed in Taiwan, Republic of China on Jul. 14, 2009, the entire contents of which are hereby incorporated by reference.

BACKGROUND OF THE INVENTION

1. Field of Invention

This invention related to a transportation device which transfers the material to cells by physical method.

2. Related Art

There are lots of ways to deliver bio-materials or medicines into cells even through skin, including using physical theorem, mechanical theorem or both of them. For instances, popular ways to administer bio-materials or medicines includes electroporation, microinjection, and the likes. But these physical injection ways are difficult to operate, and the stability and the rate of success are poor. Therefore, they are not widely used in this field. On the other hand, the research of gene guns reveals the potential for physical bio-materials or medicines transferring technique.

The method of using a gene gun is carrying the vectors (e.g. gold particles) of bio-materials (e.g. DNA) into cells by high-speed shooting for achieving gene transferring. And this technique is already extensively applied into many research fields which include plant system, cells of mammal, gene therapy, and the latest deoxyribonucleic acid (DNA) vaccine study systems as well.

For instance, the gene gun can carry gold particles mixed with DNA, put them on a cartridge, and generate seismic waves by using twinkling high-pressure stream so that the cartridge will accelerate until reaching an obstruction. Because the gold particles in the cartridge, will keep moving in a high speed due to inertia, it will enter into cells. However, the drawback of this gene gun is too noisy, and the seismic waves could kill target cells easily. This gene gun also needs to consume a large amount of expensive helium and vectors (usually gold particles).

Besides, there is another way to provide medicine by a gene gun with low pressure vapor acceleration which carries the liquid (suspension liquid with nanometer particles) with DNA to be injected into a converging-diverging nozzle directly or indirectly, and then carries the liquid into human body through the spray nozzle by the instant low pressure vapor. Although this type of gene gun is able to overcome the existing bottleneck, however, as to the existing gene gun, before the sample entering the nozzle, it forms a turbulent flow so the sample may easily have collisions with the wall and be condensed on the wall surface. Additionally, the structure design of the nozzle itself has blind angle. At the same time, low-pressure gas provides the lower kinetic energy, which can not affect the residual sample on the wall to bring it out. For the low-pressure gas accelerating gene gun, its worst drawback is that the liquid is easy to remain in the nozzle which leads to the problems of quantitative and continuous operation.

Therefore, it is an important subjective to provide a transportation device to solve existing bottlenecks encountered.

SUMMARY OF THE INVENTION

In view of the foregoing, an objective of the present invention is to provide a transportation device having the physical design of drug delivery systems based on the fluid mechanics theory for delivering the mixed material and carrier fluid to a target.

To achieve the above objective, the present invention discloses a transportation device, which can physically transport a material to a target.

The transportation device includes an input module, a transmission module and an output module.

The input module comprising a containing unit and at least one filter. The at least one filter is connected to the containing unit, and a carrier fluid that stored in the containing unit.

The transmission module is coupled to the input module. The carrier fluid and the material go through the filter and then enter the transmission module. The input module and the transmission module form at least one transmission path accordingly.

The output module has a guiding unit, a first opening, a second opening, and a throat portion positioned between the first and second openings. One end of the guiding unit is connected to the transmission module, and the other end of the guiding unit comprising a guiding corner for connecting to the first opening. The material enters the input module through the first opening and then reaches the target through the second opening.

As mentioned above, in some embodiments the transportation device of the present invention may change the fluid (including: liquid, gas, gel, etc.) size by the atomizing unit. At the same time, through a mixing unit, the atomized material or the solid particles less than 500 microns can be mixed within the carrier fluid. With applying a certain pressure (e.g. $10kg/cm^2$) in the output module, a very high-speed fluid can be generated, so that the carrier fluid and the material can be well mixed.

The temperature inside the output module may down to below zero in a fast moment, so the mixed two-phase samples can be accelerated to high speed and have instantaneous phase change (liquid to solid phase change, which includes ice crystals, ice needles, and the likes).

After he solid material is transferred to the second opening, at least a part of the solid material has phase change from solid phase to liquid phase. The liquid phase material can help to reach the surface of the targets, and the solid phase material can make it easier to enter the target (e.g. enter cells through the biological or cell surfaces), thereby achieving the purpose of transmission.

Compared with the prior art, this invention not only enhances the use of convenience of those liquid containing biological material (such as DNA, RNA, proteins, viruses, physical, chemical drugs, etc.) or solid state within 500 microns, but also can reduce the difficulty of coping and producing traditional carriers (gold grains) which could reduce the destruction to the biological material and injury to the target (for example: the target cell), and also improve the safety of using and reliable possibility. Moreover, the present invention can also control the amount of the material transferred into the target so as to enhance the dosage control.

BRIEF DESCRIPTION OF THE DRAWINGS

The invention will become more fully understood from the detailed description and accompanying drawings, which are given for illustration only, and thus are not limitative of the present invention, and wherein:

FIG. 12 is a diagram showing the internal structure of the transportation device, wherein the atomizing unit is a hydraulic atomizer.

DETAILED DESCRIPTION OF THE INVENTION

The present invention will be apparent from the following detailed description, which proceeds with reference to the accompanying drawings, wherein the same references relate to the same elements.

For enhancing the convenience of using biological material samples and the control of the output, at the same e, to reduce the difficulty of preparing the traditional carriers, the destruction of biological material, and the damage to the target. Besides, to increase the use of the safety and reliability of possibility, this invention presents a transportation device. The text below provides a detailed description and schematic together to help understand the technical features of the present invention.

Figure 1:
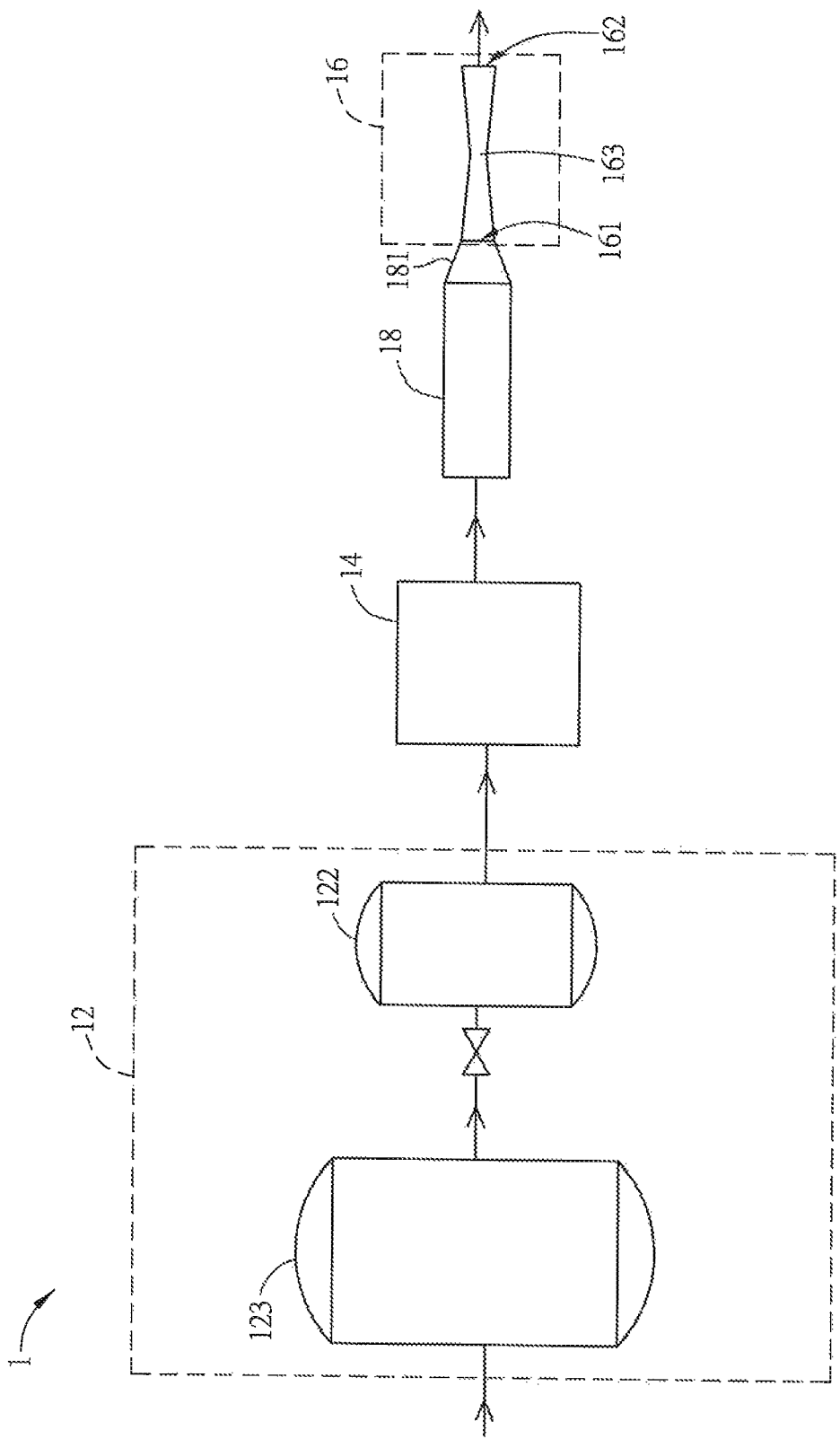
FIG. 1 is a diagram showing a transportation device according to an embodiment of the invention.
Figure 2:
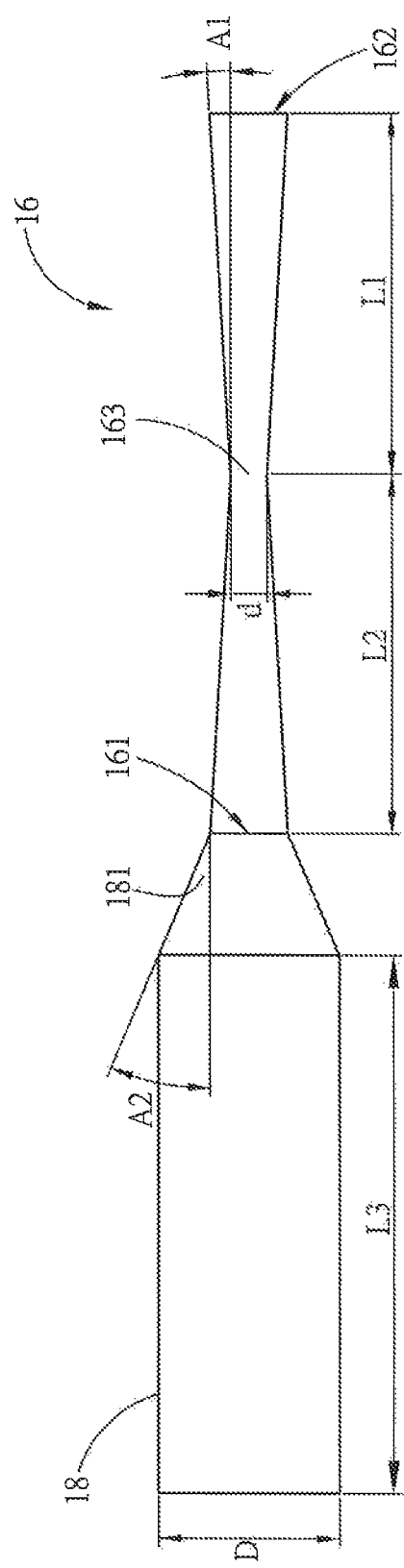
FIG. 2 is a diagram showing the structure of the guiding unit and the output module of the transportation device of the invention.
Figure 3:
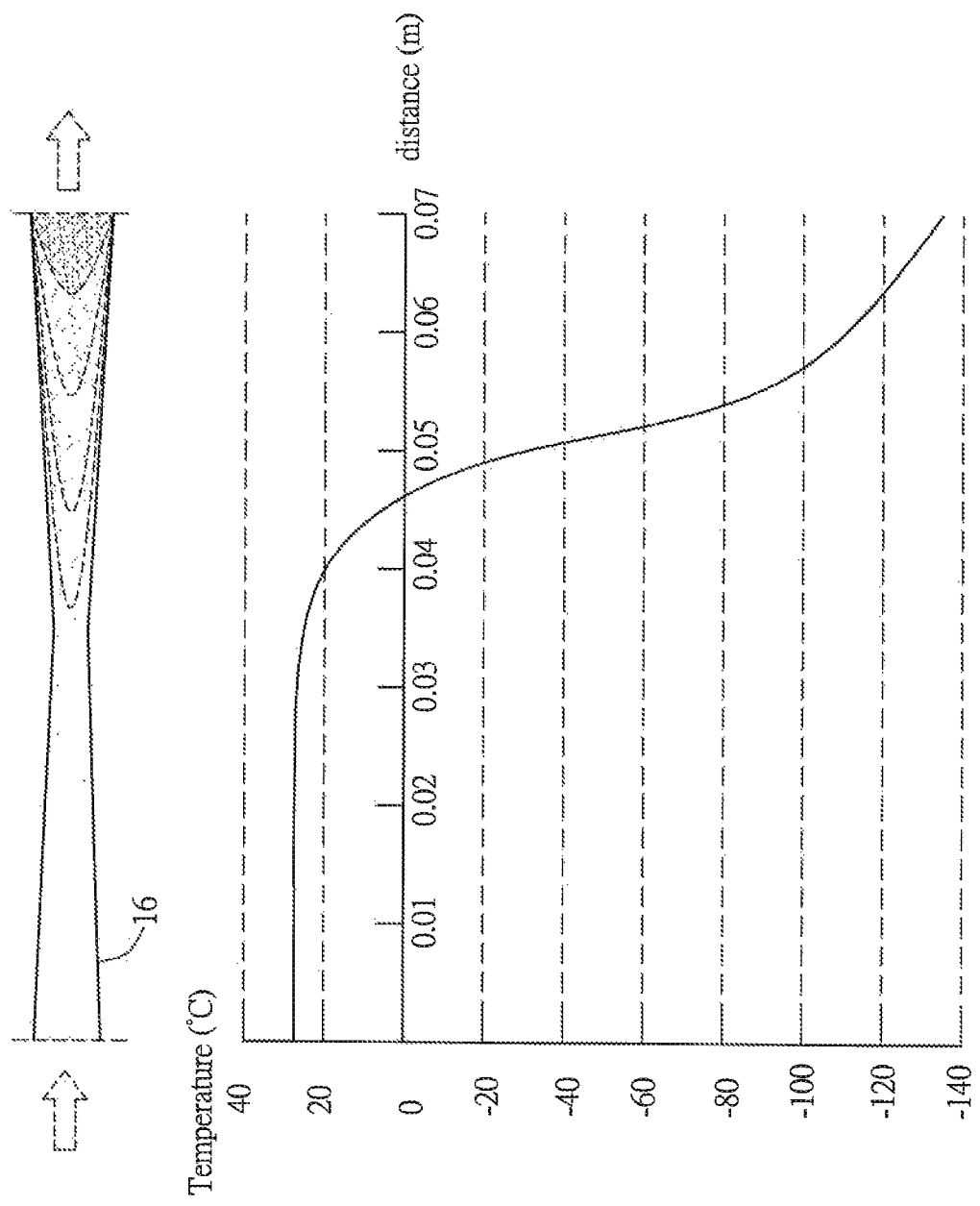
FIG. 3 is diagram showing the temperature-gradient inside the output module.

Please refer to FIG. 1-FIG. 3 together. FIG. 1 is a diagram showing a transportation device 1 according to an embodiment of the invention. FIG. 2 is a diagram showing the structure of the guiding unit and the output module of the transportation device of the invention. FIG. 3 is diagram showing the temperature-gradient inside the output module.

Referring to FIG. 1, the transportation device 1 transfers a material to a target by a physical way. The transportation device 1 includes an input module 12, a transmission module 14 and an output module 16.

The input module 12 comprising a containing unit 123 (such as gas pressure storage tank) and at least one filter 122. The purpose of the input module 12 is to provide a carrier fluid. Furthermore, the at least one filter 122 is connected to the containing unit 123, wherein a carrier fluid and the material(s) are stored in the containing unit.

The transmission module 14 is connected to the at least one filter 122 of the input module 12, receives the material(s) and the carrier fluid, and then the transmission module 14 disperses/atomizes the materials with the carrier fluid. The carrier fluid and the material(s) go through the filter 122 and then enter the transmission module 14. The input module 12 and the transmission module 14 form at least one transmission path.

The output module 16 has a first opening 161, a second opening 162, a throat portion 163, and a guiding unit 18. The material(s) enters the output module 16 through the first opening 161 and reaches the target through the second opening 162.

In addition, the aperture of the first opening 161 is larger than the aperture of the second opening 162, and the distance between the throat portion 163 and the second opening 162 is equal to or smaller than the distance between the throat portion 163 and the first opening 161. The diameter size of first opening 161 is greater than that of the second opening 162, and the mixture of the material and mass fluid enters the output module 16 through the first opening 161 and is outputted from the output module 16 through the second opening 162.

Among them, the material particle size will be less than or equal to 500 microns after dispersion/atomization, and the target of this embodiment could he cells, tissues and organs. The carrier fluid can be gas such as inert gas or air, and the material is selected from solid materials, non-solid materials, and their combinations. Herein, the non-solid materials include liquid materials, gaseous materials and colloidal material. Accordingly, the material can be dispersed in the carrier fluid to form a suspension solution, so that it can be transferred through the carrier fluid.

As shown in FIG. 2, the output module 16 is a nozzle, which includes a first opening 161, a second opening 162 and a throat portion 163 disposed between the first opening 161 and the second opening 162. The structure of the output module 16 is designed for simultaneously processing the carrier fluid and the material, so that the dispersed/atomized material and the carrier fluid can be mixed again after passing through the guiding unit 18.

In this embodiment, the aperture of the first opening 161 is larger than that of the second opening 162, and the distance L2 (mm) between the first opening 161 and the throat portion 163 is larger than the distance L1 (mm) between the second opening 162 and the throat portion 163.

More specific, the throat portion aperture is d (mm), and the distance L1 between the throat portion 163 and the second opening 162 is between three and ten times of the throat portion aperture d, which means $3d \leq L1 \leq 10d$. The second opening 162 has an expending angle A1, which is from the throat portion 163 to the second opening 162, and the expending angle A1 is between half and three times of the aperture angle of the throat portion (½d°-3d°).

The guiding unit 18 connects the first opening 161 of the output module 16 to the transmission module 14. In structural design, the opening aperture (diameter) D of the guiding unit 18 is larger than or equal to three times of the throat portion aperture d (D>3d). The length L3 of the guiding unit 18 is greater than or equal to the distance L1 between the second opening 162 and the throat 163 of the output module 16 (L3>L1). There is a guiding corner 181 configured in the conjunction of the guiding unit 18 and the output module 16. The angle A2 of the guiding corner 181 is approximately between three and fifteen times of the throat portion angle d° (3d°≤A2≤15d°). This design helps to promote the dynamic gas source (that is, carrier fluid) and the dispersed/atomized material (including non-solid particles or solid particles suspended) to have the interaction stability in the guiding unit 18. This is because there is a big gap mass density between the carrier fluid and material. Therefore, in the same pressure gradient, the acceleration (or deceleration) of the carrier fluid is more effect than the material. On the other hand, due to the configuration of the guiding corner 181, the two-phase (carrier fluid and material), after a stable interaction, can be guided by the guiding corner 181 and flow into the first opening 161 of the output module 16 without producing the residual on the wall of the guiding unit 8 due to the turbulence.

In addition, the transportation device 1 further includes a control module (not shown), which connects to the input module 12, transmission module 14 and output module 16.

More specifically, the control module is electrically connected with all modules. The control module is to control the transfer rate and time of material and carrier fluid in the input module 12, transmission module 14 and output module 16. In this embodiment, the control module is a logic circuit, which controls the transfer rate and time of the carrier fluid in the input module 12, transmission module 14 and output module 16, thereby enhancing the dosage control of transferring the material to the target.

In this embodiment, the logic circuit could control the transfer rate and time of carrier fluid transferred in the input module 12, transmission module 14 and output module 16. More specifically, the input module 12 not, only has one set or more containing units 123 The control module is composed of several mechanical or electronic control and high pressure pipelines. The purpose is to use the sophisticated electronic logic circuit to control various components of the containing unit 123 and the air loop sequence. In the containing unit 123, the power source for driving the gas is provided by the general air compressor, gas manufacture or added high-pressure gas cylinders.

For practical applications, the above-mentioned nozzle is based on the Laval Nozzle which uses very precise line geometry in order to design a converging-diverging channels, so that the flow rate of the carrier fluid can instant access to supersonic speed in the second opening 162, and take advantage of the speed of the carrier fluid to transfer its potential energy into kinetic energy and then make the carrier fluid to get instant access to rapid decline in temperature while flowing into the second opening 162.

Moreover, the material may have phase change (e.g. phase change from liquid to solid) in the nozzle. After the solid material is transferred to the second opening 162, at least a part of the solid material has phase change from solid phase to liquid phase. The liquid phase material can help to reach the surface of the targets, and the solid phase material can make it easier to enter the target, thereby achieving the purpose of transmission.

The equations relates to the isentropic flow in the nozzle are briefly described hereinbelow:

$$\frac{A_{exit}}{A_{throat}} = \frac{1}{M_{exit}}\left[\frac{2}{\gamma+1} + \frac{\gamma-1}{\gamma+1}M_{exit}^2\right]^{\frac{\gamma+1}{\gamma-1}}, \quad \text{equation (1)}$$

-continued $$\frac{P_0}{P_{exit}} = \left[1 + \frac{\gamma-1}{2}M_{exit}^2\right]^{\frac{\gamma}{\gamma-1}}, \quad \text{equation (2)}$$

$$P_{throat} = \frac{P_0}{\left(1 + \frac{\gamma-1}{2}M_{throat}^2\right)^{\frac{\gamma}{\gamma-1}}}, \quad \text{equation (3)}$$

and $$\dot{m}_{max} = \frac{P_{throat}}{RT_{throat}} M_{throat}\sqrt{\gamma RT_{throat}}\,A_{throat}. \quad \text{equation (4)}$$

Wherein, "exit" represents the second opening, "throat" represents the throat portion, M represents a Mach number, which is a ratio compared with the speed of sound, $M_{exit}$≥1, A represents the sectional area, P represents the pressure ($P_0$ represents the pressure at the first opening), and γ represents the isentropic exponent. According to the equation (1), $A_{throat}$ can be calculated by specifically selected Mach number and $A_{exit}$. According to the equation (2), $P_{exit}$ is 1 atm (normal state), so that the pressure $P_0$ of the first opening can be calculated. According to the equation (3), the pressure in the throat portion can be estimated based on the selected Mach number inside the throat portion. Consequently, the pressure values under different conditions can be obtained. To be noted, the design of the nozzle may be modified according to the actual conditions. In addition, the mass change of the material under various pressures at the throat portion can still be calculated according to the equation (4).

The temperature gradient of the output module 16 is as the curve shown in FIG. 3, wherein the X axis shows the position of the material inside the output module 16 (nozzle), and Y axis is the temperature. Therefore, by the environmental humidity and the temperature dropped rapidly, the mixture of material and carrier fluid can achieve the purpose of transmission by the formation of ice crystals or ice needles. Moreover, the mixture can penetrate through the surface of cells and then enter the cells.

In addition, in the contraction section of the nozzle, which is located between the first opening 161 and the throat portion 163, the pressure gradient is positive, the acceleration of the carrier fluid is larger than the material, and, therefore, the movement velocity of the carrier fluid will be higher than that of the material. On the contrary, in the expansion section of the nozzle, which is located between the throat portion 163 and the second opening 162, the pressure gradient is the opposite direction of the flow direction. The deceleration of the carrier fluid will enable the movement velocity of the carrier fluid less than the speed of the material. Especially when having waves in the expansion section of the throat portion 163, this deceleration will become more obvious.

Therefore, when designing the output module 16, the interaction between two fluids is considered so that the pressure and speed in the throat portion 163 can respectively reach the minimum and maximum values. When the carrier fluid in the flow field gradually accelerates to the critical state, the throat portion 163 will have choking phenomenon, and the pressure and the speed of two-phase mixture (including the carrier fluid and material) will no longer change before the throat portion 163. And when the carrier fluid flows through the throat portion 163 and enters the expansion section, the speed will still be increased instead of being decreased. It will reach its maximum, possibly over the supersonic state, at the downstream of the throat portion 163, so that the material can be dispersed/atomized into small-sized particles. Because, the dispersed/atomized material has the advantages of high speed and small size, it can penetrate through the surface of organisms or cells, and reaches the dermis or inside the cells. The transportation device of the invention can be applied to the transdermal therapeutic system, gene gun, nutrition supply device, cosmetic device, anti-aging device, etc.

The transmission module 14 will be different according to the phase of the input material, and the described material could be in solid-state, non-solid state or combination of both. The following will present a description by embodiments of the solid-state material and non-solid material.

Figure 4:
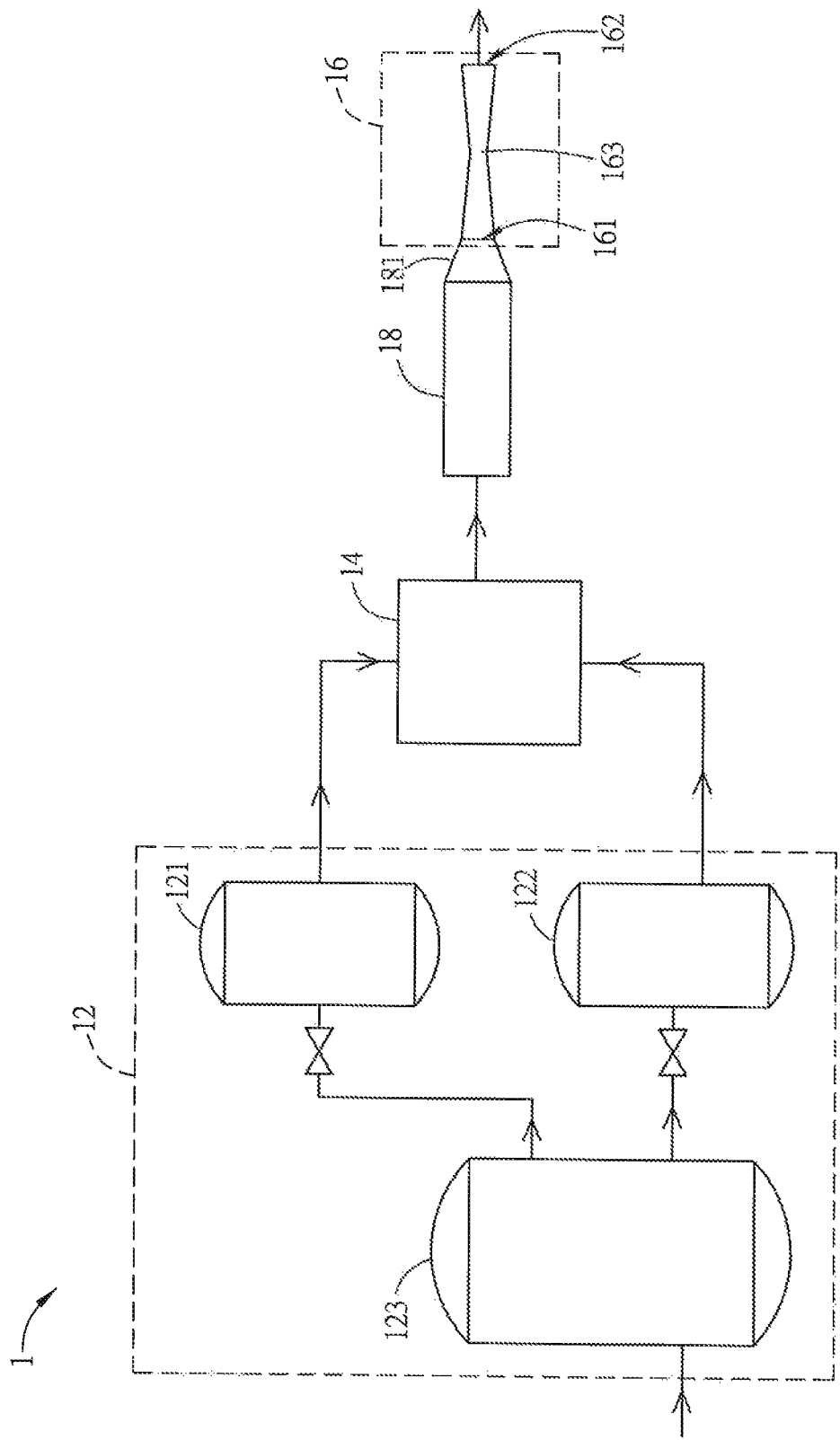
FIG. 4 is a diagram showing a transportation device according to another embodiment of the invention.

Next, please refer to FIG. 4, which is a diagram showing a transportation device according to another embodiment of the invention. Different from the previous embodiment, in present embodiment, the at least one filter comprising two filters which are a first filter 121 and a second filter 122 (the degree of filtering down to 0.5 microns or less)

As depicted, the first and the second filters 121, 122 are respectively connected to the containing unit 123 and the transmission module 14 to form two transmission paths. The two transmission paths are independent from each other, which is the two transmission paths do not interlaced and does not need to be synchronous.

Other elements and the relationship between these elements are described in the previous embodiment, therefore will not be repeated herein.

Figure 5:
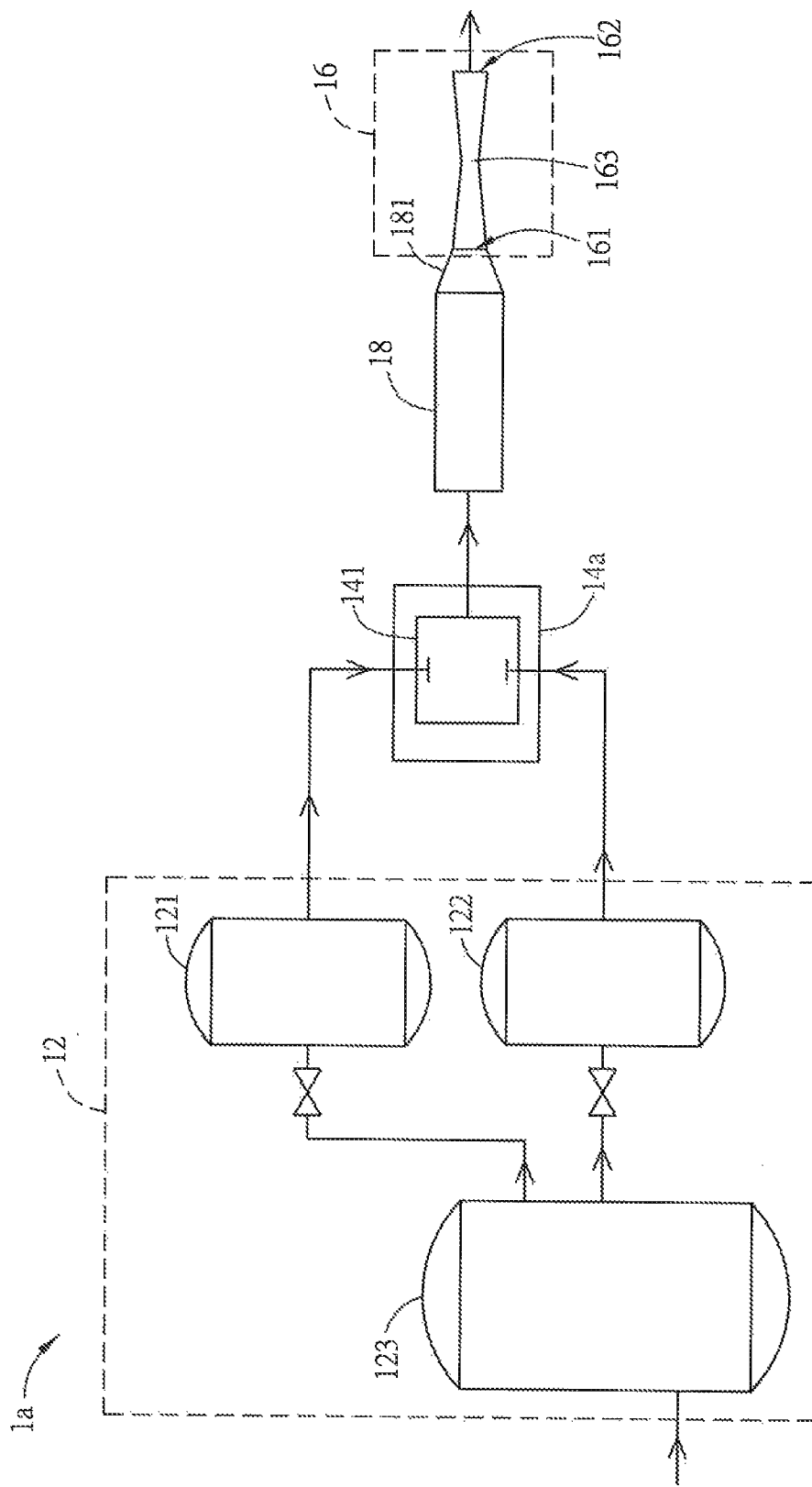
FIG. 5 is a diagram showing the transportation device used for solid material.
Figure 6A:
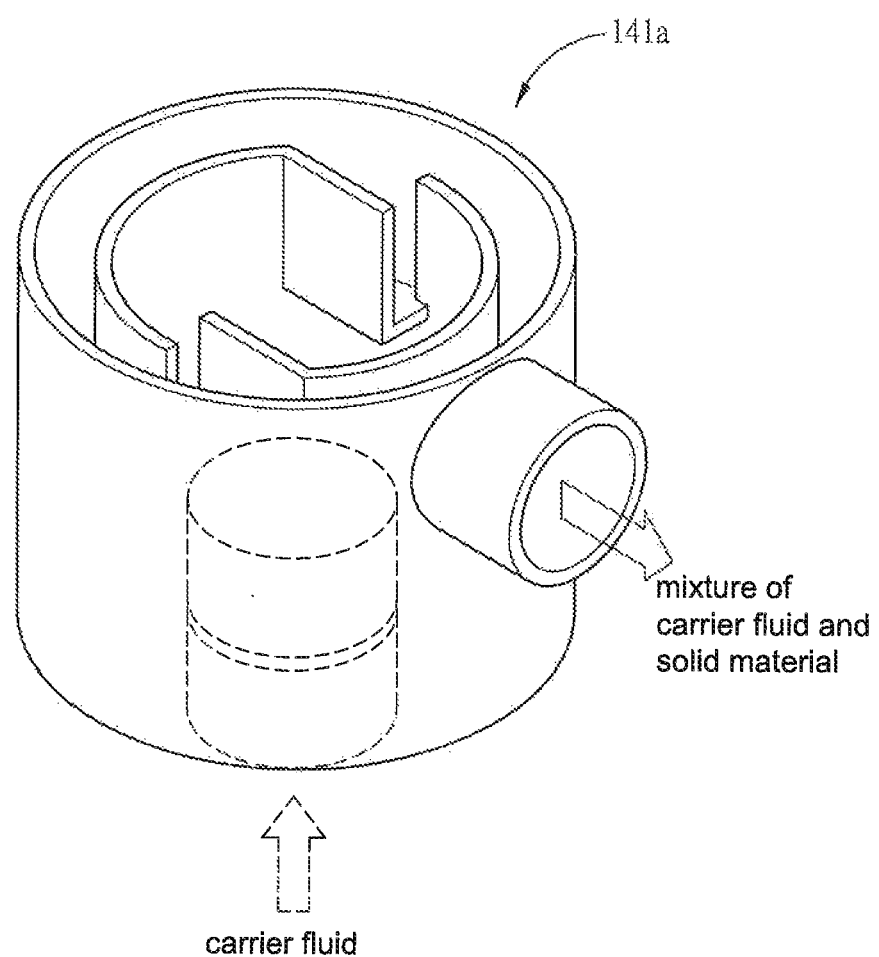
FIG. 6A is diagram showing the internal structure of a mixing unit of the transportation device used for solid material.

Then, please refer to FIG. 5 and FIG. 6A, FIG. 5 is a diagram showing the transportation device used for solid material, and FIG. 6A is diagram showing the internal structure of a mixing unit of the transportation device used for solid material.

FIG. 5 and FIG. 6A shown an example of applying solid material (e.g. the powder of chemical compound.) The transportation device 1a of this embodiment is similar to the above-mentioned transportation device 1. The difference is that the transportation device 1a includes a transmission module 14a, which further includes a mixing unit 141 (or 141a in FIG. 6A.) The mixing unit 141 is connected to the input module 12 and the guiding unit 18. The referred solid-state material can be stored in the mixing unit 141 in advance, or it can be supplied by a feeding unit (not shown) in batch or continuously to the mixing unit 141 of the transmission module 14a. The mixing unit 141 receives the compressed carrier fluid and combines the solid-state material and the carrier fluid. Then, the compressed carrier fluid can push the mixture of the carrier fluid and the material out of the mixing unit 141.

In addition, the mixing unit 141 can be used as a storage tank, so that the valves (not shown) of the mixing unit 141 can control the flow rate of the mixture to the output module 16. The mixture of the solid-state material and carrier fluid enters the output module 16 through the first opening 161 and is outputted from the output module 16 through the second opening 162. Obviously, the transportation device 1a transfers the solid material, and the solid material can be stored in the mixing units 141 directly if the solid material, which is selected to have a particle size smaller than or equal to 500 microns, does not need additional atomization.

To be noted, the mixing unit 141 not only can mix the solid-state material and the carrier fluid, but also can make these materials homogeneously suspended in the carrier fluid, so that the solution of the solid-state material and carrier fluid can keep the suspension state in the mixing unit 141 without forming precipitation at the bottom of mixing unit 141 before outputting. The way to output the mixed solid-state material and carrier fluid from the mixing unit 141 can be carried out by mechanical or electronic control valve.

Figure 6B:
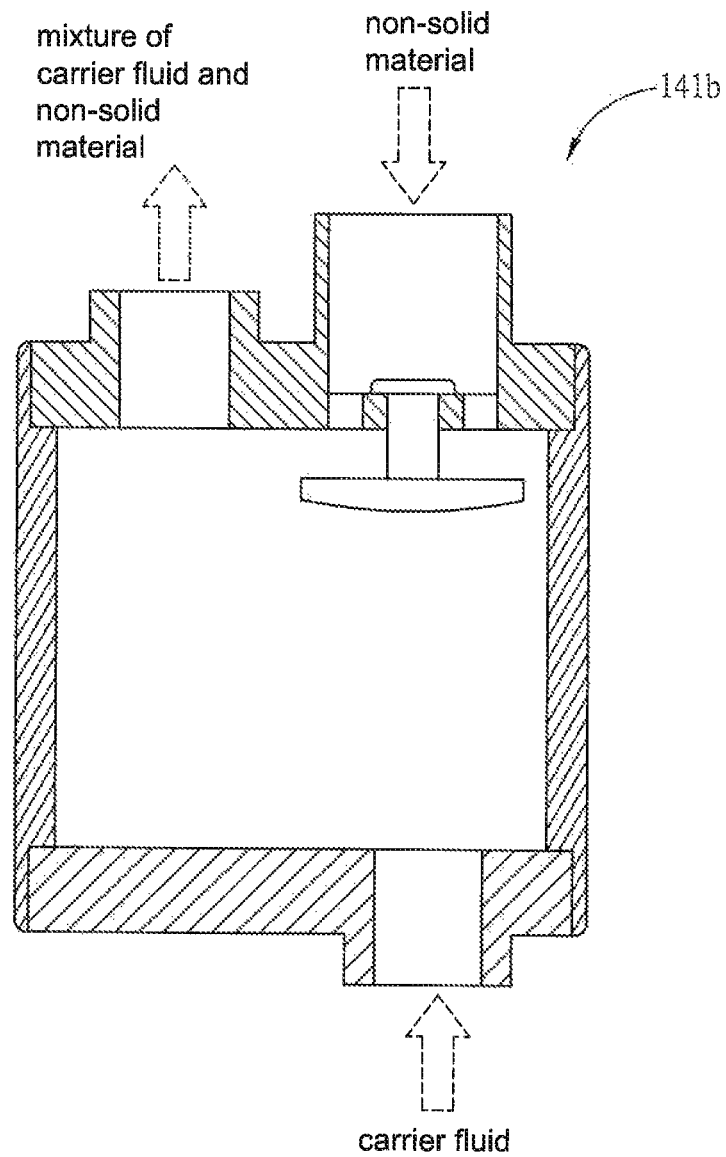
FIG. 6B is diagram showing the internal structure of a mixing unit of the transportation device used for non-solid material.
Figure 7A:
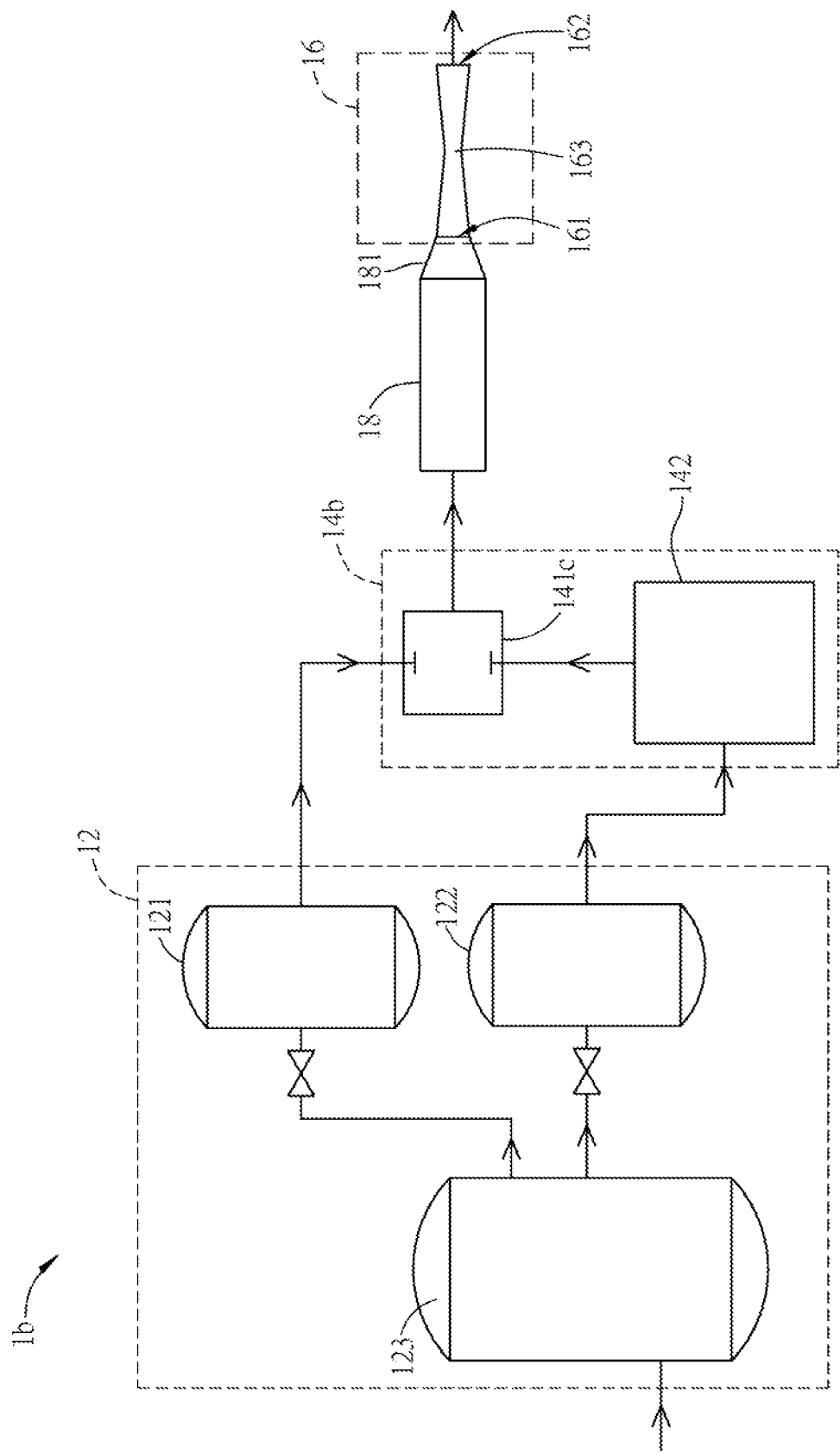
FIG. 7A and FIG. 7B are diagrams showing the transportation device used for non-solid material.

Alternatively, if the material is a non-solid-state material, such as a liquid or gel material, the transportation device of another embodiment is shown in FIG. 6B and FIG. 7A. FIG. 6B is diagram showing the internal structure of a mixing unit of the transportation device used for non-solid material, and FIG. 7A is a diagram showing the transportation device used for non-solid material.

The transportation device 1b of this embodiment is similar to the transportation device 1 of the above-mentioned embodiment. The different is in that the transportation device 1b includes a transmission module 14b, which further includes an atomizing unit 142 and a mixing unit 141c (or 141b in FIG. 6B.)

Compared with the previous embodiment applied to the solid-state material, the transportation device 1b of this embodiment is configured with the atomizing unit 142, which is connected to the input module 12. The referred non-solid material can be stored in the atomizing unit 142 in advance and is then dispersed/atomized by the carrier fluid, or it can be supplied by a feeding unit (not shown) in batch or continuously to the atomizing unit 142 of the transmission module 14b. The particle size of the non-solid material should be smaller than or equal to 500 microns.

Otherwise, the mixing unit 141c is connected to the input module 12, the atomizing unit 142, and the guiding unit 18. The mixing unit 141c can serve as a storage tank for store the mixed carrier fluid and the non-solid material, so that the valves (not shown) of the mixing unit 141c can control the flow rate of the mixture and output the mixture to the guiding unit 18 driven by the continuously supplied carrier fluid.

Then, the mixture of the non-solid material and the carrier fluid enters the output module 16 through the guiding unit 18 and the first opening 161 and is outputted from the output module 16 through the second opening 162. After being atomized by the atomizing unit 142, the size of the non-solid material is smaller than or equal to 500 microns.

The difference with the above-mentioned embodiment is that the material in this embodiment is non-solid materials, which include liquid materials, colloidal materials and gaseous materials. In order to enable the particle size of the above-mentioned non-solid material to be physically reduced, the non-solid materials need to be atomized by the atomizing unit 142 before mixing up with the carrier fluid. In more detailed, to "atomize" the solid or non-solid material is to separate or break it by physical method so as to decrease the particle size of the material.

With regarding to a liquid material, the atomization can be used to achieve the purpose of the dispersion or atomization. In this embodiment, the material is a liquid material for example. The mentioned atomizing unit 142 could be an electrical-oscillated atomizer, twin-fluid atomizer or hydraulic atomizer.

Figure 7B:
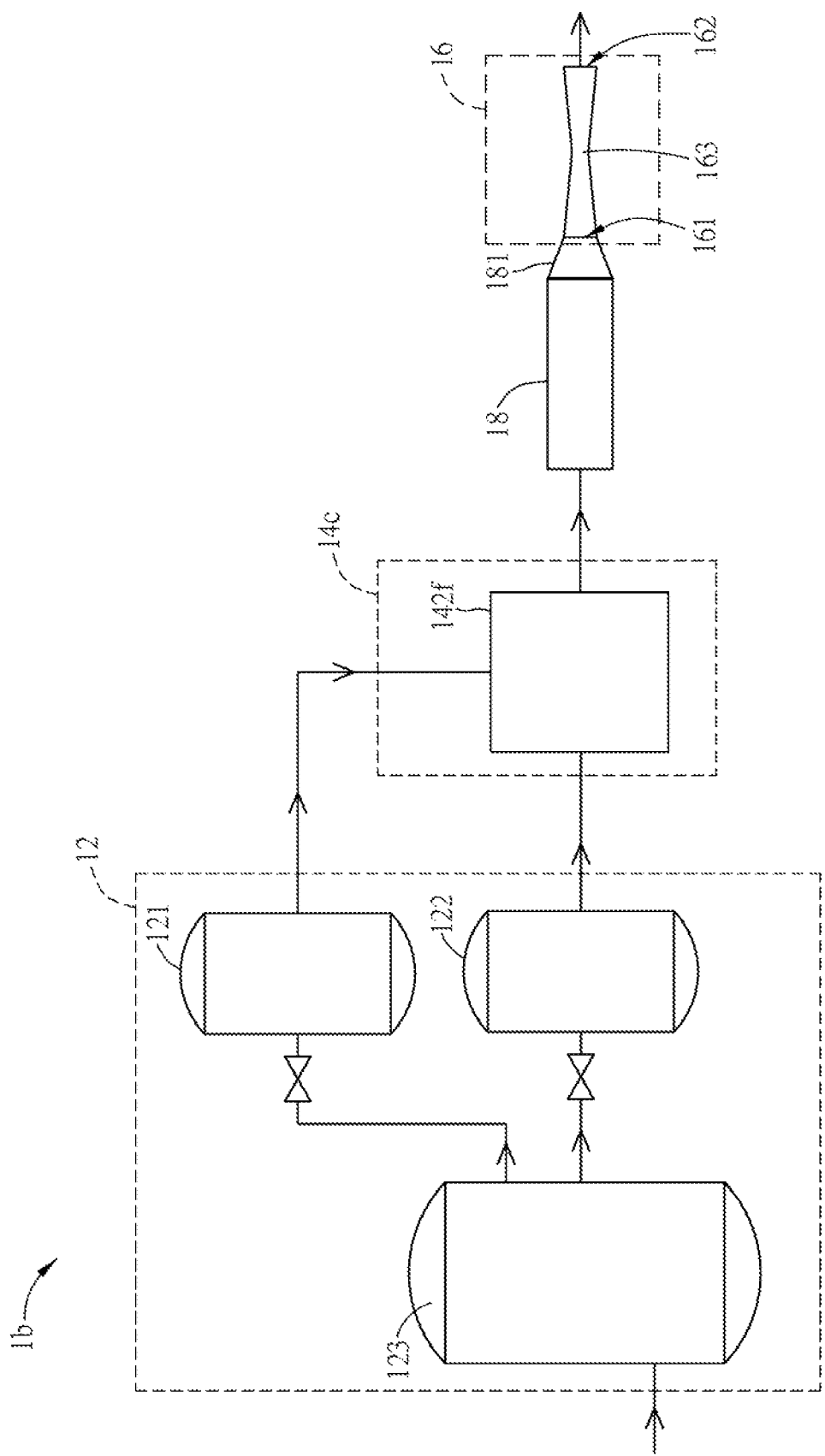

FIG. 7B is a diagram showing the transportation device used for non-solid material. The transportation device 1b in FIG. 7B is similar to the transportation device 1b in FIG. 7A. The different is in that the atomizing unit 142 is a twin-fluid atomizer 142f.

Figure 8:
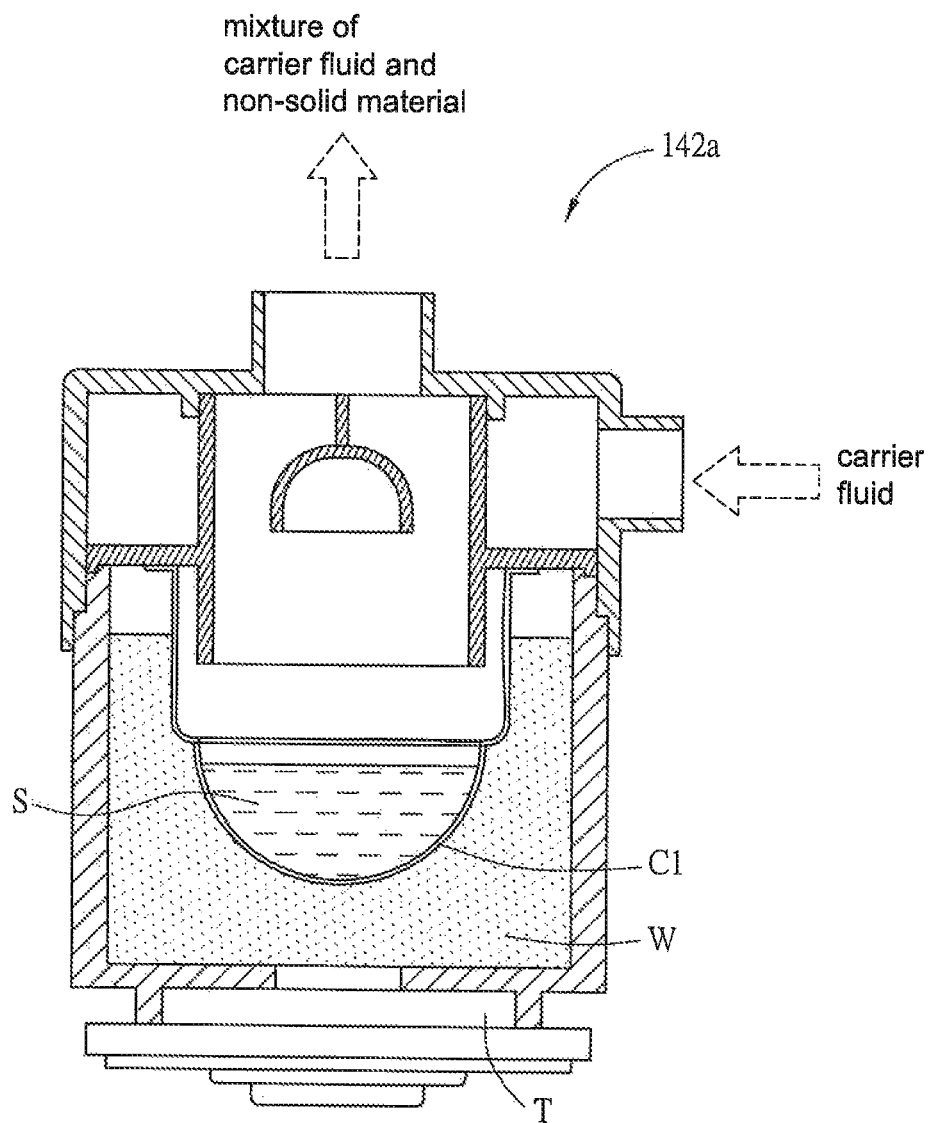
FIG. 8 is a diagram showing the internal structure of the transportation device, wherein the atomizing unit is an electrical-oscillated atomizer.

FIG. 8 is a diagram showing the internal structure of the transportation device, wherein the atomizing unit is an electrical-oscillated atomizer.

More specifically, when the atomization unit 142 is an electrical-oscillated atomizer 142a, because the fluid atomization mechanism of the electrical-oscillated atomizer 142a is using the electronic shock principle, the pressure lens power oscillator T is used to generate high-frequency waves (ultrasonic) to atomize the fluid into mist.

By the mode of vibration risers, that is, placing the non-solid material S in a container C1 with water W, a total shock is produced by the use of electronic high-frequency waves (ultrasonic) to make the non-solid material S transform into a mist of fog particles. The interesting part is that the size of the atomized particle through the above-mentioned approach is about 0.5 to 6 microns. However, the non-solid material S using the above-mentioned approach should be an electronic conductive fluid.

Figure 9:
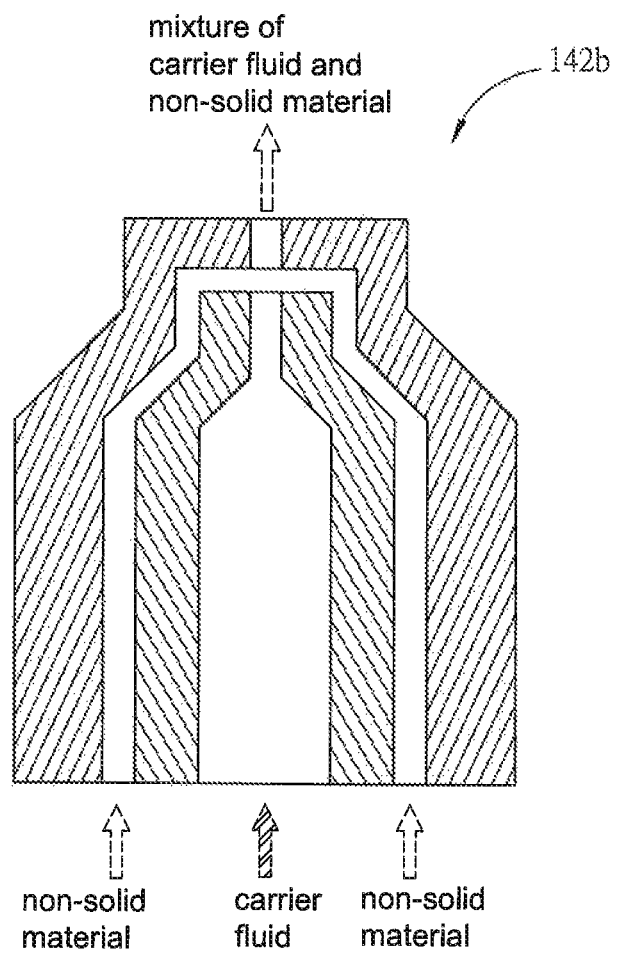
FIG. 9 is a diagram showing the internal structure of the transportation device, wherein the atomizing unit is a twin-fluid atomizer.

FIG. 9 is a diagram showing the internal structure of the transportation device, wherein the atomizing unit is a twin-fluid atomizer. When the atomizing unit 142 is a twin-fluid atomizer 142b (as shown in FIG. 9), because the liquid atomization mechanism of the twin-fluid atomizer 142b uses the high-speed principle of the compressed carrier fluid (e.g. air) and the Bernoulli's principle, the mixture of the non-solid material and carrier fluid can be atomized into very small particles by using the flow speed and pressure after flowing through the output module 16 (e.g. nozzle), and the aerosol particle size is about 10.0 microns.

Figure 10:
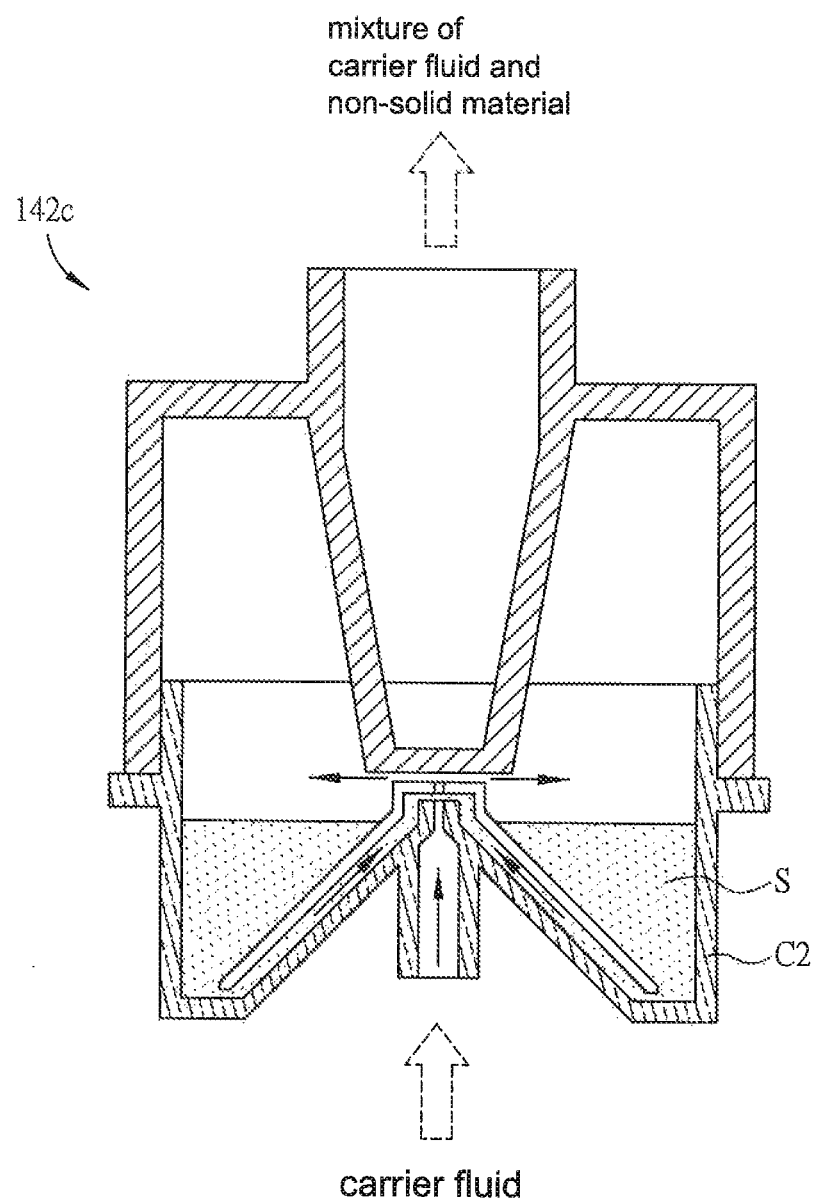
FIG. 10 is a diagram showing the internal structure of the transportation device, wherein the atomizing unit is a parallel-type twin-fluid atomizer.

In addition, based on the liquid atomization mechanism of the twin-fluid atomizer 142b, the containers for storing the non-solid material can be divided into parallel type and vertical type. FIG. 10 is a diagram showing the internal structure of the transportation device, wherein the atomizing unit is a parallel-type twin-fluid atomizer 142c. The parallel-type twin-fluid atomizer 142c uses the compressed carrier fluid in a state of high-speed flow, and when the compressed carrier fluid flows into the output module 16 (take nozzle as an example here), because an instant vacuum is generated once the carrier fluid flows through the output module 16, and the compressed carrier fluid can hit the non-solid material so as to generate spoiler in the container C2, the non-solid material will be guided out. Then, the compressed carrier fluid and the non-solid material S is mixed together to form a twin fluid, so the non-solid material S outputted from the output module 16 will be atomized and formed very small mist particles. In this case, the non-solid material S is, for example but not limited to, a fluid.

Figure 11:
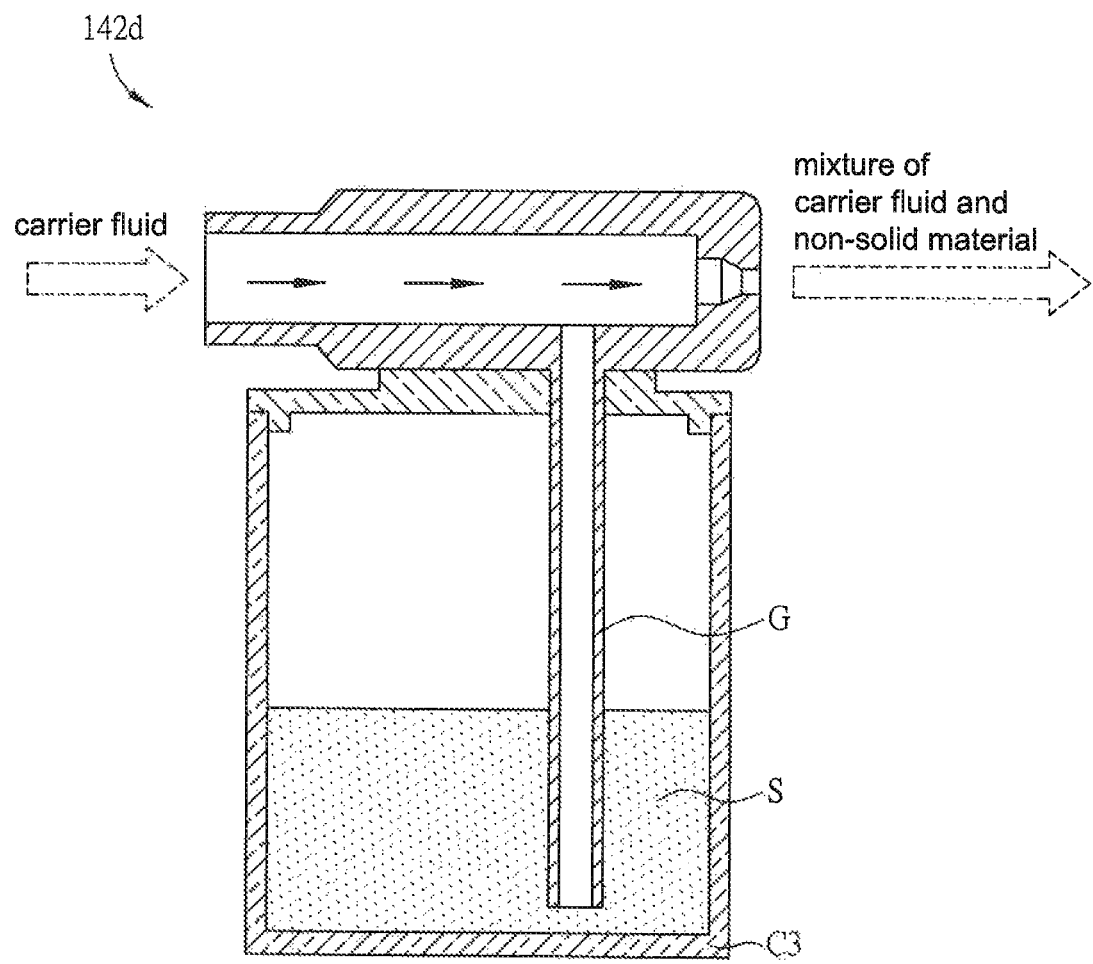
FIG. 11 is a diagram showing the internal structure of the transportation device, wherein the atomizing unit is a vertical-type twin-fluid atomizer.

FIG. 11 is a diagram showing the internal structure of the transportation device, wherein the atomizing unit is a vertical-type twin-fluid atomizer. In this case, the vertical-type twin-fluid atomizer 142d uses the Bernoulli's principle which means the principle of large flow gets small pressure. Therefore, the pressure on the export is small due to the rapid outflow of the carrier fluid, and this can cause the non-solid material S to be attracted and sucked out of the container C3 through the pipe G. Then, the non-solid material S can be atomized to form very small mist particles by the output module 16. In this case, the non-solid material S is, for example but not limited to, a fluid.

Figure 12:
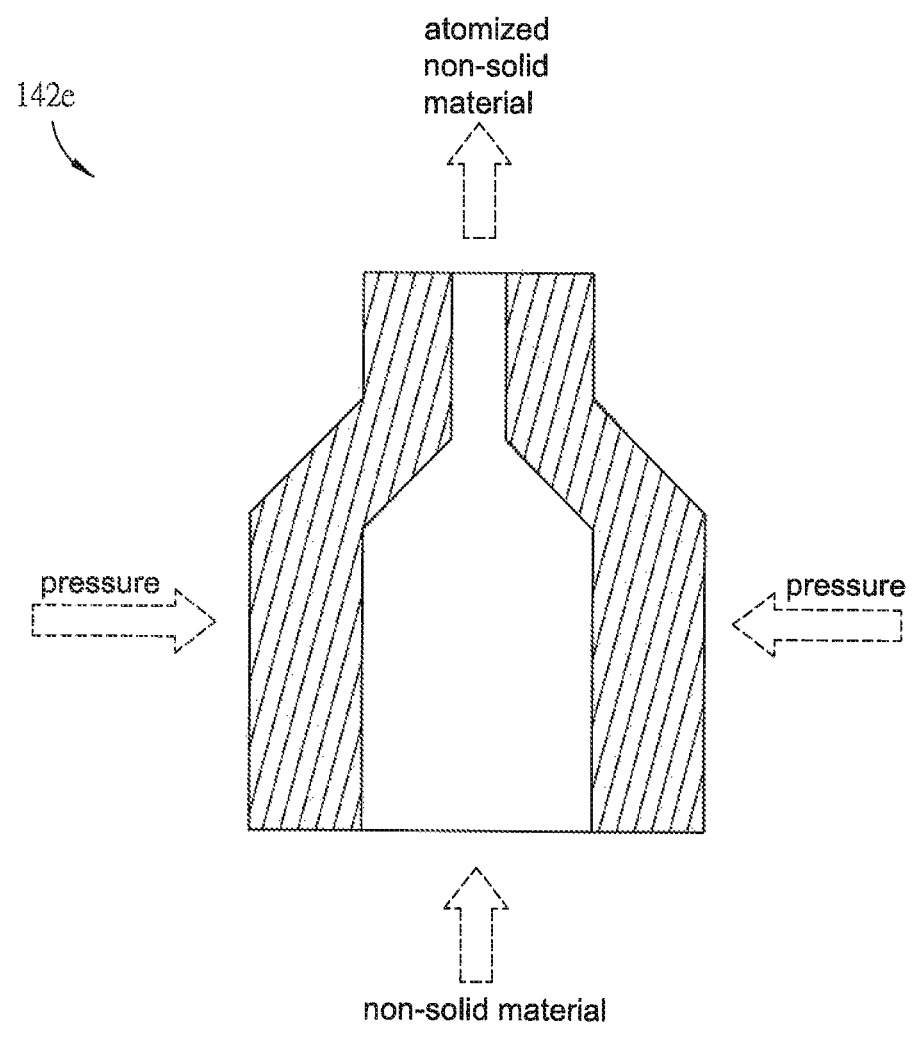

FIG. 12 is a diagram showing the internal structure of the transportation device, wherein the atomizing unit is a hydraulic atomizer 142e. In this case, because the hydraulic atomizer 142e uses the external strength to provide pressure to the solid-state materials, due to the pressure difference, the non-solid materials can be directly atomized through the output unit 16 to form very small mist particles.

To sum up, the transportation device of the present invention may change the fluid (including: liquid, gas, gel, etc.) size by the atomizing unit.

At the same time, through the mixing unit, the atomized material or the solid particles less than 500 microns can he mixed within the carrier fluid. With applying a certain pressure (e.g. 10 kg/cm$^2$) in the output module, a very high-speed fluid can be generated, so that the carrier fluid and the material can be well mixed.

The temperature inside the output module may down to below zero in a fast moment, so the mixed two-phase samples can be accelerated to high speed and have instantaneous phase change (liquid to solid phase change, which includes ice crystals, ice needles, and the likes).

After the solid material is transferred to the second opening, at least a part of the solid material has phase change from solid phase to liquid phase. The liquid phase material can help to reach the surface of the targets, and the solid phase material can make it easier to enter the target (e.g. enter cells through the biological or cell surfaces), thereby achieving the purpose of transmission.

Compared with the prior art, this invention not only enhances the use of convenience of those liquid containing biological material (such as DNA, RNA, proteins, viruses, physical, chemical drugs, etc.) or solid state within 500 microns, but also can reduce the difficulty of coping and producing traditional carriers (gold grains) which could reduce the destruction to the biological material and injury to the target (for example: the target cell), and also improve the safety of using and reliable possibility. Moreover, the present invention can also control the amount of the material transferred into the target so as to enhance the dosage control.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A transportation device, transporting a material to a target, comprising:
   an input module, comprising a containing unit and at least one filter, the at least one filter being connected to the containing unit, wherein a carrier fluid and the material are stored in the containing unit;
   a transmission module coupled to the at least one filter of the input module, wherein the carrier fluid and the material go through the filter and then enter the transmission module, and the input module and the transmission module form at least one transmission path;
   a guiding unit, connecting to the transmission module and comprising a guiding corner; and
   an output module, comprising a first opening, a throat portion and a second opening, the throat portion being positioned between the first opening and the second opening, the first opening being connecting to the guiding corner, wherein the material enters the output module through the first opening, passes through the throat portion and reaches the target through the second opening,
   wherein the pressure gradient from the first opening to the throat portion is positive, the acceleration of the carrier fluid is larger than the material, and the movement velocity of the carrier fluid is higher than that of the material, wherein the pressure gradient from the throat portion to the second opening is negative, the deceleration of the carrier fluid is larger than the material, the movement velocity of the carrier fluid is less than the that of the material, so the temperature of the carrier fluid rapidly declines below 0° C.

2. The transportation device according to claim 1, wherein an aperture of the first opening is larger than an aperture of the second opening, the distance between the throat portion and the second opening is equal to or smaller than the distance between the throat portion and the first opening and is between three and ten times of an aperture of the throat portion, and the second opening has an expending angle which is between half and three times of an aperture angle of the throat portion.

3. The transportation device according to claim 2, wherein the length of the guiding unit is longer than or equal to the distance between the throat portion and the second opening, the size of the end connected to the transmission module is three times larger than the size of the throat portion, and an angle of the guiding corner is between three and fifteen times of the aperture angle of the throat portion.

4. The transportation device according to claim 1, wherein the at least one filter comprising two filters which are a first filter and a second filter, and the first and the second filters are connected between the containing unit and the transmission module to form two transmission paths.

5. The transportation device according to claim 1, wherein the carrier fluid is gas.

6. The transportation device according to claim 5, wherein the carrier fluid is an inert gas or air.

7. The transportation device according to claim 1, wherein the transmission module further comprises:
a mixing unit connecting to the input module and the guiding unit.

8. The transportation device according to claim 1, wherein the transmission module comprises:
an atomizing unit connecting to the input module.

9. The transportation device according to claim 1, further comprising:
a supplying unit connecting to the transmission module for providing the material to the transmission module.

10. The transportation device according to claim 8, wherein the atomizing unit is an electrical-oscillated atomizer, a twin-fluid atomizer, or a hydraulic atomizer.

11. The transportation device according to claim 8, wherein after the material is atomized by the atomizing unit, the particle size of the atomized material is equal to or less than 500 microns.

12. The transportation device according to claim 1, further comprising:
a control module connecting to the input module, the transmission module and the output module.

13. The transportation device according to claim 1, wherein the output module is a nozzle.

\* \* \* \* \*